United States Patent [19]
Ramin et al.

[11] 4,022,065
[45] May 10, 1977

[54] CALIBRATED SAMPLE DELIVERY APPARATUS ACCOMMODATING OFFSET ERROR

[76] Inventors: James A. Ramin, 2802 White Oak, Houston, Tex. 77007; Stanley D. Stearns, 7812 Bobbitt, Houston, Tex. 77055

[22] Filed: Feb. 19, 1976
[21] Appl. No.: 659,373
[52] U.S. Cl. .................................. 73/422 GC
[51] Int. Cl.² ............................... G01N 1/10
[58] Field of Search ..................... 73/422 GC

[56] References Cited
UNITED STATES PATENTS
3,827,303  8/1974  Shiina .................. 73/422 GC Primary Examiner—S. Clement Swisher
Attorney, Agent, or Firm—Donald Gunn

[57] ABSTRACT

A sample measuring apparatus is disclosed. In the preferred embodiment, a syringe having a set of calibrations is used to collect a specimen. The syringe has a set of calibrations which are offset from actual zero. The extent of offset accommodates the connecting volume found in a sample injection valve between the end of the syringe's outlet and the front of the portion of the sample actually injected. This enables the sample to be injected into a high resolution liquid chromatography column when an injection valve is switched. This enables the injection of a specified calibrated sample. Moreover, sufficient sample is injected to overcome the connecting volume or offset occurring in the injection valve where a connecting volume in the valve captures and holds a certain portion of the specimen. This connecting volume is held to a practical minimum.

10 Claims, 2 Drawing Figures

U.S. Patent    May 10, 1977    4,022,065
FIG.1
FIG.2
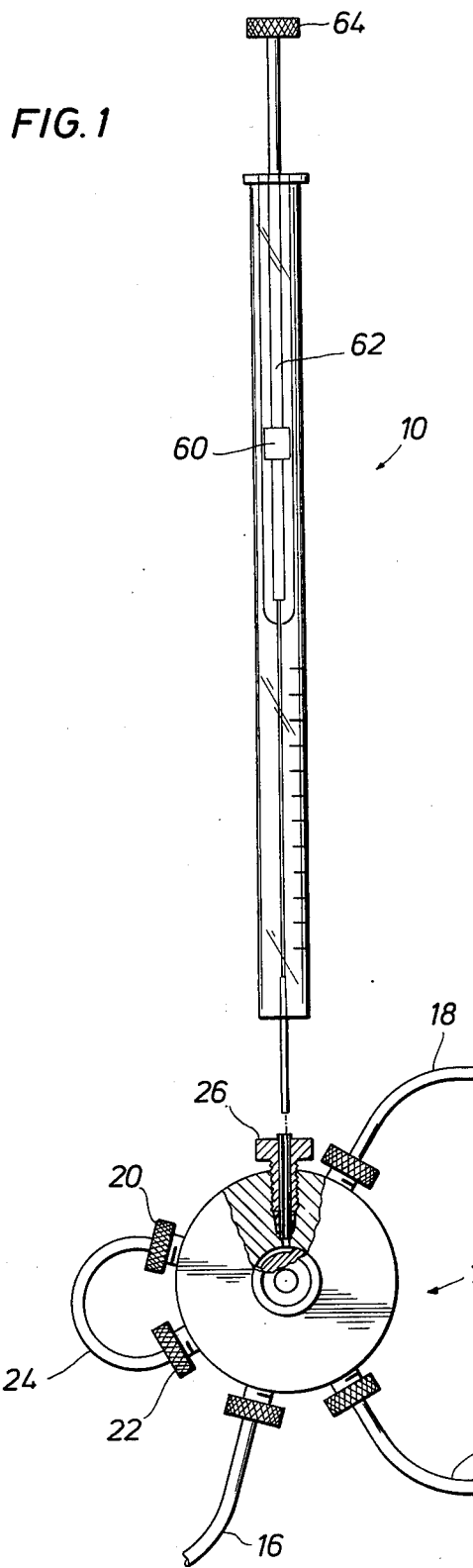
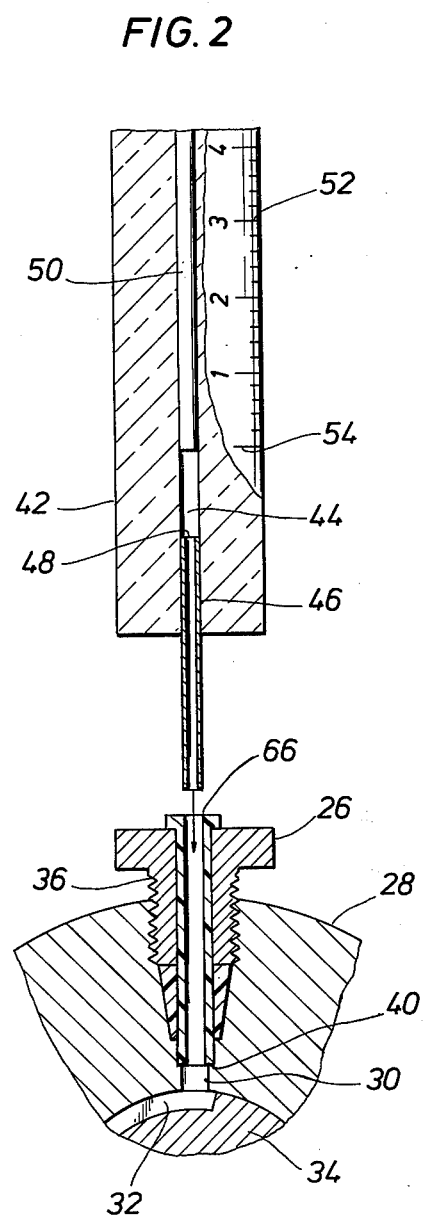

CALIBRATED SAMPLE DELIVERY APPARATUS ACCOMMODATING OFFSET ERROR

BACKGROUND OF THE INVENTION

In the testing of samples, it is necessary normally to deliver a specified volume of a sample into a test apparatus so that the quantitative data obtained from the test apparatus is meaningful. Where the source of the specimen is generous, it is of no major consequence that some portion of the sample is spilled or otherwise wasted. Some wastage is desirable because this helps assure that the test apparatus has a full sized, metered specimen input to it. By way of contrast however, many chemicals exist in such minute quantities that it is foolish to waste any of the sample. As an example, sophisticated medical research involving test animals which are relatively small may create a specimen which is distinctly small. For instance, in the investigation of hormonal problems in small test animals such as rabbits or guinea pigs, or in other problems too numerous to exemplify, the material obtained for testing may be extremely small and minute. Accordingly, there is not enough of the material to fill a standard sample loop. Sample loops are normally installed with sample injection valves connected at the input of a chromatographic test device. A sample loop will typically hold from about 10 microliters to 10 milliliters of a sample. When the sample available is smaller than the precise volume of the loop, difficulties arise in the delivery of the sample from some sort of source or carrier into the sample injection valve.

Sample injection syringes have been used heretofore. They have met with some success. However, they have been limited in that it is difficult to transfer a small sample (smaller than the standard loop available) into the loop. The apparatus of the present invention has overcome this problem. This apparatus has overcome the problem by taking into account the offset error which would occur upon using a conventionally configured syringe to inject into a sample injection valve.

The sample injection valves are normally manufactured with a rotatable plug in the valve body, there being a number of ports or passages in the valve body which deliver the specimen into the sample loop. The sample loop is normally connected between two specified ports of the valve. When the measured specimen is delivered through an inlet port and flows through passages in the sample injection valve, a portion of it ends up in certain connecting spaces between the inlet port and the sample loops. When the plug is rotated, a portion of the sample is not transferred.

It has been discovered that a sample injection syringe having a set of offset calibrations which has an offset equal to the volume between the end of the syringe needle or inlet tube and the front of the sample in the valve (having the form of connecting space) is advantageously used. As a consequence, the apparatus of the present invention is able to deliver a sample which differs from the size of the standard sample loop. Nevertheless, the sample is delivered into the loop and is precisely known or measured by the sample injecton syringe. Moreover, the offset which occurs in the operation of the valve is overcome so that the metered quality of sample delivered into the sample loop is controlled.

SUMMARY OF THE INVENTION

This invention is a sample injection syringe having a set of calibrations which are offset from zero. The amount of offset enables this syringe to fill by an amount larger than the calibrations which amount is equal to the connecting volume within a sample injection valve. The syringe is used with an inlet port and fitting on the valve body which delivers the sample to passages communicated with the rotatable plug of the sample injection valve. The sample is routed then into the sample loop. The apparatus can be used with the sample loop fully filled or only partly filled, the size of the specimen having previously been measured and indicated on the injection syringe. Of course, when the sample loop is filled, the sample size is determined with the maximum possible precision. If the sample loop is only partly filled, the sample size is indicated by the specially offset syringe calibrations.

DESCRIPTION OF THE DRAWINGS

FIG. 1 is a sectional view of the apparatus of the present invention showing an injection syringe and the sample injection valve cooperatively arranged and connected with a chromatographic test apparatus, not shown; and FIG. 2 is an enlarged sectional view of the lower end of the syringe and the fitting of the injection valve.

DESCRIPTION OF THE PREFERRED EMBODIMENT

Attention in first directed to FIG. 1 of the drawings where a sample injection syringe is indicated by the numeral 10. It is cooperative with a sample injection valve 12. The valve is connected to a chromatographic column by a conduit 14. The column is of the typical construction and it performs liquid chromatography testing on the sample at back pressures typically ranging from 100 psi to 7000 psi. The test apparatus is mentioned inasmusch as it constitutes a portion of the supportive equipment which the present invention is used with. However the test apparatus does not form any portion of the disclosed invention. To this end, the sample valve includes the conduit 14 which is connected to the column and a conduit 16 from a pump which provides a liquid carrier. In addition, a conduit 18 is connected to a drain.

The sample injection valve 12 incorporates a first port 20 and a second port 22. These ports are connected together by a calibrated standard sample loop. The size of the sample loop is subject to variation; typical measures are in the range of about 10 microliters to about 10 milliliters. The size is not critical. The significant point is that a sample loop is incorporated which, taking into acccount the ports and passages within the valve 12, stores and receives, when full, a standard sized sample.

The numeral 26 identifies a sample injection port. It communicates into the valve body 28 (see FIG. 2) and opens into an internal passage 30. The passage 30 opens into a movable port 32 in the plug valve 34. The plug element is rotatable by means of a shaft and upon rotation, it moves the port 32 from the injection port 26. Any liquid in the passage 32 is rotated by the rotatable plug and then delivered into the standard sample loop 24. If the standard sample loop is filled, this is well and good. However, this apparatus also provides a calibrated sample which is smaller than the standard sample loop and which will only partly fill it.

In FIG. 2, the fitting 26 is shown to incorporate a set of threads 36 which thread it into the valve body 28. An axial passage opens through the fitting 26 and is aligned with internal passage 30. The passage 30 is relatively smaller and hence defines an upwardly facing shoulder 40. The shoulder 40 limits the travel of the fitting 26. It also limits the penetration of the syringe equipment to be described.

The syringe 10 incorporates a glass body 42. It is preferably transparent. It has an axial passage 44. A syringe needle 46 is embedded in the glass body 42 by techniques known in the art. The syringe needle 46 defines an upper shoulder 48. The shoulder 48 limits the downward travel of a plunger 50. When the syringe is filled, the plunger is raised. The plunger itself is sized to fit in the axial passage 44. As it moves downwardly, it forces any liquid in the axial passage out of the syringe and through the needle 46. The syringe itself further includes a set of calibration at 52. The calibrations 52 extend along the side. It will be observed that the zero calibration mark at 54 is offset. It is offset from the shoulder 48. The volume of liquid between the shoulder 48 and the zero calibration mark will represent the offset volume as defined herein. The offset volume serves a purpose to be described.

In FIG. 1 of the drawings, the syringe body is shown to include an enlargement 60 on a plunger shaft 62. The plunger shaft 62 extends to a knurled knob 64 which can be grasped and pushed by the user on injecting a sample from the syringe 10.

The syringe is provided with the needle 46. When inserted, the needle is preferably surrounded by a flexible tubing 66. The tubing fits snuggly around the needle and the syringe abuts the top curled lip so that there is no leakage between the two at the point. The needle 46 inserts into the tubing limited by the shoulder 40. The tubing 66 barely fits within the fitting 26 and is enlarged at the lower end to fill the opening above the shoulder. It extends to the passage 30 and bottoms out at the shoulder 40 and axial pressure on the tubing 66 causes it to seal against the valve body. The flexible tubing 66 thus prevents leakage along the exterior of the fitting 26. All liquid ejected from the syringe must flow from the needle 46 into the passage 30. The size of the passage 30 is best held constant for valves of a given size; this enables the use of one size of offset syringe. However, the syringe offset can be varied for valves of differing manufacture or size, or indeed, the offset can be mentally noted and subtracted if the syringe is used with a different valve.

The passage 30 comprises a connecting volume. The offset volume of the syringe is made equal to the total connecting volume. The passage in the movable valve element which is injected is part of the loop volume. As will be observed on viewing the enlarged view of FIG. 2, the passage 32 rotates with the plug; that portion of the sample which is delivered into the passage 30 but does not flow from it is not delivered into the test equipment. The offset volume of the syringe thus accommodates this error (the connecting volume). This error exists as a result of the manner in which the valve is constructed and the syringe fits into it. It is possible in theory but impractical in practice to decrease the size of the passage 30 to zero. With this in mind, the apparatus functions in the following manner.

Assume that the sample loop 24 is calibrated for 10 microliters. Assume further that the passage 30 represents a connecting volume of 0.8 microliters. In light of these assumptions, the offset volume above the shoulder 48 in the syringe to the zero calibration 54 matches the connecting volume of the passage 30, or 0.8 microliters. If the amount of the specimen available is 6 microliters, in actuality the first 0.8 milliliters stored in the syringe is the offset volume. The user then will measure the remaining portion of his sample, and will note the size of the sample by using the calibrations along the side of the syringe 10. When this has been done, the user is then ready to deliver the sample into the sample loop 24.

The valve is operated to isolate the port 26 against back pressure. The flexible tubing 66 and plug 26 are threaded into the valve body until they are squared up against the shoulder 40. In the assembled state, the sample is ejected by positioning the syringe in the fitting. As the sample is ejected, it is pumped into the valve and flows into the passages of the valve (dependent on sample size) and partly or wholly fills the sample loop 24. After it has been delivered, the valve 12 is switched by rotating the plug. This rotates the plug and thereby isolates the fitting 26 from the pressure of the test equipment. A portion of the sample is left in the passage 30 representing the connecting volume. The calibrated or measured sample delivered past the passage 30 is isolated to flow in the chromatographic test system. Should the sample be smaller than the sample loop 24, the user has its actual measure. The comparison of the actual measure of the sample (by a simple ratio to the maximum volume of the sample loop 24) then provides a scale factor for the data obtained from the chromatographic equipment.

It is preferable to keep the syringe engaged with the sample injection valve 12 in the manner shown in FIG. 2 until after the valve has been operated to isolate the injection past. Then, the syringe can be removed. The syringe can be left in the loading port 26 indefinitely after operation.

As with any injection system, it is necessary to purge the loading port 26 prior to its next use. Typically, a mobile phase solvent is used to insure that all residual traces of the previous sample which might have been captured in the connecting volume at 30 or removed. After flushing with some type of solvent, the second or any number of subsequent uses of the illustrated can proceed.

The foregoing is directed by the preferred embodiment but the scope is determined by the claims which follow.

We claim:

1. A sample injection apparatus for use with a sample injection valve having multiple ports, one port being a sample injection port which valve incorporates an internal passage of specified volume extending to a movable valve element wherein the internal passage is a part of a connecting volume which connecting volume represents that volume of a specimen supplied to said sample injection valve which is not supplied by the valve on operation of the valve at the time that a sample is transferred thereby, and wherein said valve is adapted to be connected to a sample test apparatus and the valve is further operable between at least two positions, one position enabling injection of a sample into said sample injection port, and the other of said positions isolating said sample injection port on operation of said valve element and wherein the valve cooperates with an apparatus comprising:
a sample injection syringe, said syringe having a needle which inserts into the port of a valve and which syringe is adapted to receive, store and measure against a set of calibrations thereon a volume of sample.

2. The apparatus of claim 1 wherein said syringe includes an axial passage, a plunger therein for pushing liquid therefrom, a shoulder in said passage defining the limits of travel of said plunger, and a zero point for the set of calibrations thereon, said axial passage having a specified volume between said shoulder and the zero point on the set of calibrations which is equal to the connecting volume within said sample injection valve.

3. The apparatus of claim 2 wherein said injection syringe includes a hollow needle embedded in the body thereof axially communicated with the axial passage of aid syringe and said needle is hollow, and further including a flexible tubular member sized to fit snuggly about the needle in a leakproof seal and which flexible tubing inserts into said injection port of said valve.

4. The apparatus of claim 3 wherein said injection port includes a transverse shoulder which limits the penetration of said flexible tubular member.

5. The apparatus of claim 4 wherein said flexible tubular member fits in said port in a sealed connection.

6. The apparatus of claim 3 wherein said sample injection valve includes a plug valve element which is rotatable and which valve element rotates in a valve body whereupon rotation of said plug interrupts flow through said inlet port thereof.

7. The apparatus of claim 1 wherein said calibrations are offset from zero volume in said sample injection syringe by an amount equal to the connecting volume.

8. A sample injection valve for use with a sample injection syringe, said syringe being adapted to receive, store and measure a specified volume of sample comprising:
a sample injection valve having multiple ports, one port being a sample injection port into the valve which valve incorporates an internal passage of specified volume extending to a movable valve element wherein the internal passage is a part of a connecting volume which connecting volume represents that volume of a specimen supplied to said sample injection valve which is not delivered by the valve on operation of the valve at the time that a sample is transferred thereby, and wherein said valve is adapted to be connected downstrem to a sample test apparatus;
a shoulder in said port which is cooperative with an axially located seal means, said shoulder limiting entry of said injection syringe and said seal means preventing leakage along the syringe and
said valve further being operable between at least two positions, one position enabling injection of a sample into said sample injection port, and the other of said positions isolating said sample injection port on operation of said valve element.

9. The apparatus of claim 8 wherein said sample injection valve includes a rotatable element and which valve element rotates in a valve body whereupon rotation of said plug interrupts flow through said inlet port thereof.

10. A sample injection apparatus comprising:
a sample injection valve having multiple ports, one port being a sample injection port which valve incorporates an internal passage of specified volume extending to a movable valve element wherein the internal passage is a part of a connecting volume which connecting volume represents that volume of a specimen supplied to said sample injection valve which is not supplied by the valve on operation of the valve at the time that a sample is transferred thereby, and wherein said valve is adapted to be connected to a sample test apparatus;
said valve further being operable between at least two positions, one position enabling injection of a sample into said sample injection port, and the other of said positions isolating said sample injection port on operation of said valve element; and
a sample injection syringe, said syringe being adapted to receive, store and measure against a set of calibrations a volume of sample wherein said calibrations are offset from zero volume in said sample injection syringe by an amount equal to the connecting volume.

* * * * *